(12) United States Patent
Liu et al.

(10) Patent No.: US 11,576,768 B2
(45) Date of Patent: Feb. 14, 2023

(54) STENT GRAFT

(71) Applicant: LIFETECH SCIENTIFIC (SHENZHEN) CO., LTD, Guangdong (CN)

(72) Inventors: Caiping Liu, Shenzhen (CN); Benhao Xiao, Shenzhen (CN)

(73) Assignee: LIFETECH SCIENTIFIC (SHENZHEN) CO., LTD., Shenzhen (CN)

( * ) Notice: Subject to any disclaimer, the term of this patent is extended or adjusted under 35 U.S.C. 154(b) by 0 days.

(21) Appl. No.: 16/956,070

(22) PCT Filed: Dec. 11, 2018

(86) PCT No.: PCT/CN2018/120319
§ 371 (c)(1),
(2) Date: Jun. 19, 2020

(87) PCT Pub. No.: WO2019/128701
PCT Pub. Date: Jul. 4, 2019

(65) Prior Publication Data
US 2021/0093439 A1 Apr. 1, 2021

(30) Foreign Application Priority Data
Dec. 27, 2017 (CN) .......................... 201711446248.8

(51) Int. Cl.
*A61F 2/86* (2013.01)
*A61F 2/07* (2013.01)
*A61F 2/06* (2013.01)

(52) U.S. Cl.
CPC ....................................... *A61F 2/07* (2013.01)

(58) Field of Classification Search
CPC .... A61F 2/07; A61F 2250/0039; A61F 2/915; A61F 2/89; A61F 2/2418;
(Continued)

(56) References Cited

U.S. PATENT DOCUMENTS 6,423,090 B1 * 7/2002 Hancock ................. A61F 2/915
623/1.15
6,893,458 B2 * 5/2005 Cox ......................... A61F 2/91
623/1.15
(Continued)

FOREIGN PATENT DOCUMENTS

CN 2822554 Y 10/2006
CN 201438978 U 4/2010
(Continued)

OTHER PUBLICATIONS

First Search dated Mar. 25, 2020 in corresponding Chinese Application No. 2017114462480; 2 pages.
(Continued)

*Primary Examiner* — Ann Schillinger
(74) *Attorney, Agent, or Firm* — Maier & Maier, PLLC (57) ABSTRACT

A stent graft, including multiple wavy rings. The stent graft includes, in a circumferential direction, a region A and a region B connected to the region A. Each wavy ring includes a first wavy section located in the region A, and a second wavy section located in the region B. The wave included angle of the first wavy section is about 70°-120°; the ratio of the wave height of the first wavy section to the spacing between adjacent first wavy sections is 1/4-3; the wave included angle of the second wavy section is 30°-60°, the ratio of the wave height of the second wavy section to the spacing between adjacent second wavy sections is 1/4-3/2, and the ratio of the wave height of the first wavy section to the wave height of the second wavy section is greater than or equal to 1/3 and less than 1.

10 Claims, 8 Drawing Sheets

(58) Field of Classification Search
CPC .. A61F 2002/91508; A61F 2002/91516; A61F 2002/19525; A61F 2/91; A61M 31/00; A61M 31/002
See application file for complete search history.

(56) References Cited

U.S. PATENT DOCUMENTS

| | | | | |
|---|---|---|---|---|
| 8,663,313 | B2 * | 3/2014 | Boismier | A61F 2/915 623/1.15 |
| 2001/0010013 | A1 * | 7/2001 | Cox | A61F 2/91 623/1.11 |
| 2004/0073290 | A1 * | 4/2004 | Chouinard | A61F 2/91 623/1.15 |
| 2004/0073291 | A1 * | 4/2004 | Brown | A61F 2/915 623/1.34 |
| 2004/0230293 | A1 | 11/2004 | Yip et al. | |
| 2005/0049667 | A1 * | 3/2005 | Arbefeuille | A61F 2/844 623/1.11 |
| 2005/0278017 | A1 * | 12/2005 | Gregorich | A61F 2/88 623/1.44 |
| 2006/0015173 | A1 * | 1/2006 | Clifford | A61F 2/91 623/1.38 |
| 2006/0235505 | A1 * | 10/2006 | Oepen | A61F 2/915 623/1.15 |
| 2007/0055345 | A1 * | 3/2007 | Arbefeuille | A61F 2/07 623/1.13 |
| 2008/0004690 | A1 * | 1/2008 | Robaina | A61F 2/915 623/1.42 |
| 2008/0114441 | A1 * | 5/2008 | Rust | A61F 2/07 623/1.13 |
| 2009/0069880 | A1 | 3/2009 | Vonderwalde et al. | |
| 2010/0152835 | A1 * | 6/2010 | Orr | A61F 2/86 623/1.15 |
| 2010/0198333 | A1 * | 8/2010 | Macatangay | A61F 2/88 623/1.15 |
| 2014/0243951 | A1 | 8/2014 | Orr | |
| 2014/0277340 | A1 * | 9/2014 | White | A61F 2/954 623/1.11 |
| 2014/0277391 | A1 * | 9/2014 | Layman | A61F 2/89 623/1.32 |
| 2014/0296975 | A1 | 10/2014 | Tegels et al. | |
| 2015/0018933 | A1 * | 1/2015 | Yang | A61F 2/07 623/1.14 |
| 2015/0250626 | A1 * | 9/2015 | Fischer | B21F 1/04 623/1.13 |
| 2017/0128189 | A1 * | 5/2017 | Wang | A61F 2/07 |
| 2019/0000606 | A1 * | 1/2019 | Shu | A61F 2/97 |
| 2019/0015227 | A1 * | 1/2019 | Xiao | A61F 2/86 |
| 2020/0315820 | A1 * | 10/2020 | Guo | A61F 2/848 |

FOREIGN PATENT DOCUMENTS

| | | |
|---|---|---|
| CN | 103598929 A | 2/2014 |
| CN | 104586536 A | 5/2015 |
| CN | 104905892 A | 9/2015 |
| CN | 205019198 U | 2/2016 |
| CN | 107242917 A | 10/2017 |
| CN | 109966034 A | 7/2019 |
| EP | 3 064 171 A1 | 9/2016 |
| EP | 3 075 352 A1 | 10/2016 |
| EP | 3 733 126 A1 | 11/2020 |
| JP | 2007125274 A | 5/2007 |
| WO | 2019/128701 A1 | 7/2019 |

OTHER PUBLICATIONS

Extended Search Report dated Jan. 21, 2021 in corresponding European Application No. 18897536.1; 7 pages.
Office Action dated Apr. 1, 2020 in corresponding Chinese Application No. 201711446248.0; 16 pages.
Indian Office Action dated Jun. 16, 2021, in connection with corresponding IN Application No. 202027029220 (6 pp.).
International Search Report dated Feb. 27, 2019 and Written Opinion in corresponding International application No. PCT/CN2018/120319; 11 pages.

* cited by examiner

STENT GRAFT

FIELD

The embodiments relate to the field of medical apparatuses, in particular to a stent graft.

BACKGROUND

Over the past decade, endovascular stent-grafts for aortic dissections have been widely used in lesions such as thoracic and abdominal aortic aneurysms and arterial dissections, and have become a first-line treatment with definite efficacy, less trauma, faster recovery and fewer complications. However, for special lesions such as aortic arch, celiac trunk, bilateral renal artery or superior mesenteric artery, the use of stent grafts can affect the blood supply to the arterial branch vessels. In view of this situation, the stent graft is usually opened in situ by laser or mechanical means during the operation, so that the stent graft produces an expected hole, and then the branch stent is transported to the hole and docked with the stent graft. Such therapeutic regimen overcomes the dependence on the anatomical structure of human branch vessels.

In the prior art, when a stent graft is opened in situ, there are often problems that the window size is difficult to meet the requirements, or the window edge support is poor.

SUMMARY

The embodiments provide a stent graft suitable for in-situ fenestration to overcome the defects in the prior art.

In order to overcome the defects in the prior art, the solutions of the embodiments are as follows:

Provided is a stent graft, including a plurality of wavy rings. The stent graft includes, in a circumferential direction, a region A and a region B connected with the region A; each wavy ring includes first wavy segments located in the region A and second wavy segments located in the region B; a wave included angle of each first wavy segment ranges from 70° to 120°; the ratio of a wave height of the first wavy segment to a spacing between the adjacent first wavy segments ranges from 1/4 to 3; a wave included angle of each second wavy segment is 30°-60°; the ratio of a wave height of the second wavy segment to a spacing between the adjacent second wavy segments is 1/4-3/2; and the ratio of the wave height of the first wavy segment to the wave height of the second wavy segment is greater than or equal to 1/3 and less than 1.

In the stent graft, the region A includes a greater curvature side region and a lesser curvature side region that are distributed in the circumferential direction, the wave included angle of the greater curvature side region is 80°-100°, and the wave included angle of the lesser curvature side region is 75°-95°.

In the stent graft, the ratio of the wave height of the first wavy segment in the greater curvature side region to the wave height of the first wavy segment in the lesser curvature side region is 0.7-1.

In the stent graft, the ratio of the wave spacing between the adjacent first wavy segments in the greater curvature side region to the wave spacing between the adjacent first wavy segments in the lesser curvature side region is 0.7-1.

In the stent graft, the greater curvature side region and the lesser curvature side region are symmetrically disposed in the circumferential direction, and the region B is located between the greater curvature side region and the lesser curvature side region.

In the stent graft, the ratio of the area covered by the greater curvature side region on an outer surface of the stent graft to the area covered by the lesser curvature side region on the outer surface of the stent graft is 0.7-1.3.

In the stent graft, the included angle of the region B in the circumferential direction is 15°-90°.

In the stent graft, when a connecting line between a wave crest of the first wavy segment and a corresponding wave crest of the adjacent first wavy segment is parallel to a busbar of the stent graft, the value of L1/L2 is greater than or equal to 1/3 and less than or equal to 1, and L1 is greater than or equal to 4 mm and less than or equal to 12 mm. In the present invention, the "busbar" denotes the longitudinal line along the axial direction of the stent.

In the stent graft, when a connecting line between the wave crest of the first wavy segment and a corresponding wave trough of the adjacent first wavy segment is parallel to the busbar of the stent graft, the value of L1/L2 is greater than or equal to 1/4 and less than or equal to 3/4, and L1 is greater than or equal to 4 mm and less than or equal to 14 mm.

In the stent graft, the wave height of the first wavy segment is 3-15 mm, and the wave height of the second wavy segment is 8-18 mm.

Thus, the stent graft for in-situ fenestration has the following beneficial effects, with the arrangement of the region A and the region B with different wave included angles in the circumferential direction of the stent graft, and the adjustment on the ratio of the wave height of the region A to the wave height of the region B, the region A can meet the requirements of fenestration, and the region B can meet the requirement of axial supporting force, so that the stent graft is prevented from shortening into a tumor cavity. In addition, by adjusting the ratio of the wave height to the wave spacing of the region A and the ratio of the wave height to the wave spacing of the region B, the requirements of fenestration can be well met in each position of the region A, the adaptability of the stent graft is improved, and meanwhile, the situation that the bending property of the stent graft in the position is affected due to dense distribution of local waves in the region A and the region B, or the situation that the stent graft is prone to deformation due to poor the supporting effect of the stent graft in the position caused by sparse distribution of local waves in the region A and the region B, is avoided.

BRIEF DESCRIPTION OF THE DRAWINGS

The embodiments will be further described in combination with accompanying drawings. In the drawings.

DETAILED DESCRIPTION OF THE EMBODIMENTS

In order that the technical features, objects and effects of the embodiments may be more clearly understood, various embodiments thereof will now be described in detail with reference to the accompanying drawings.

It should be noted that "distal" and "proximal" are used as orientation words, which are customary terms in the field of interventional medical apparatuses, where the "distal" means an end away from an operator during a surgical procedure, and the "proximal" means an end close to the operator during the surgical procedure. An axial direction refers to a direction which is parallel to the connecting line of a distal center and a proximal center of a medical apparatus; a radial direction refers to a direction perpendicular to the axial direction; and the distance from the axis refers to the distance reaching the axis in the radial direction.

Figure 1:
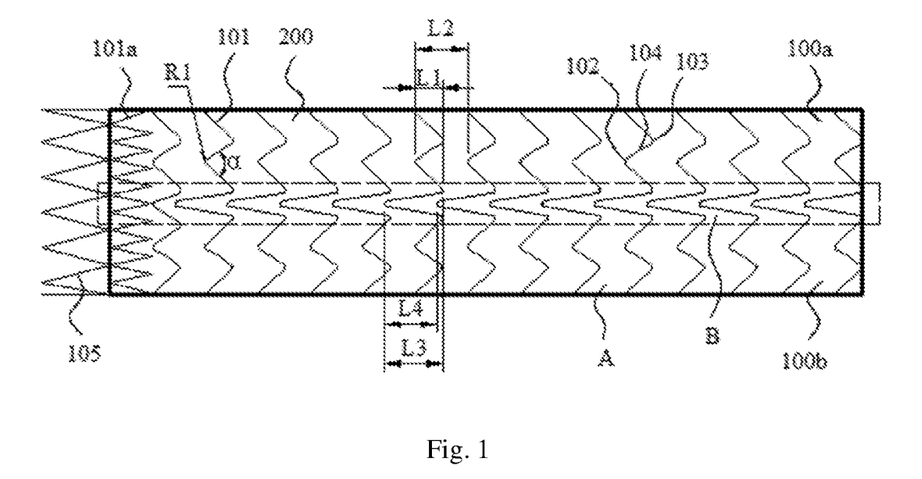
FIG. 1 is a schematic diagram of a straight tubular stent graft provided by a first exemplary embodiment.

As shown in FIG. 1, a first exemplary embodiment provides a stent graft which is substantially an open-ended and hollow tubular structure, the stent graft including a plurality of wavy rings 101, and covering membranes 200 fixed to the plurality of the wavy rings 101 to connect the plurality of the wavy rings 101.

The covering membranes 200 are substantially middle-closed and open-ended tube cavity structures and made of high molecular materials having good biocompatibility, such as e-PTFE, PET, or the like. The covering membranes 200 are fixed to the plurality of wavy rings 101 and enclosed to form a tube cavity with a longitudinal axis, and the tube cavity serves as a channel through which blood flows when the stent graft is implanted in a blood vessel.

The wavy rings 101 are made of materials with good biocompatibility, such as nickel titanium, stainless steel, or the like. The plurality of wavy rings 101 are arranged sequentially from a proximal end to a distal end, such as being arranged in a parallelly spaced manner. The embodiment does not limit a specific arrangement of the plurality of wavy rings 101, and the plurality of wavy rings 101 may be connected into a mesh-like structure. Each wavy ring 101 is a closed cylindrical structure, and includes a plurality of proximal vertexes 102, a plurality of distal vertexes 103, and supporting bodies 104 connecting the adjacent proximal vertexes 102 and distal vertexes 103, and the proximal vertexes 102 and distal vertexes 103 are wave crests and troughs of corresponding waves, respectively. The plurality of wavy rings 101 have the same or similar wavy shapes, for example, the wavy rings 101 may be Z-shaped wave, M-shaped wave, V-shaped wave or sinusoidal wave structures, or other structures that are radially compressible to a small diameter.

The stent graft may be prepared as follows: weaving a metal wire into a required wave shape, where the metal wire may be a nickel-titanium alloy wire with a wire diameter of, for example, 0.35 mm; and, after heat setting, sleeving two end portions of the metal wire with a steel jacket and fixing by mechanical pressing so that the metal wire and the steel jacket are connected and fastened to form a metal ring. After all the wavy rings 101 are manufactured, surfaces of the wavy rings 101 which are sequentially arranged are covered with membranes. For example, inner surfaces and outer surfaces of the plurality of wavy rings 101 may be integrally covered with e-PTFE membranes, the plurality of wavy rings 101 are located between two covering membranes 200, and the e-PTFE covering membranes of an inner layer and an outer layer are bonded together by high-temperature pressing, thereby fixing the plurality of wavy rings 101 between the two covering membranes. In other embodiments, the wavy rings 101 may also be sutured to PET membranes.

Additionally, when formed by integrally cutting a metal tube, the wavy rings 101 are not required to be fixedly connected by the steel jacket. Alternatively, the wavy ring may be formed by welding two end points of the metal wire.

Referring to FIG. 1, the stent graft includes, in a circumferential direction, a region A and a region B connected with the region A, where a region surrounded by dotted lines in FIG. 1 is the region B. The wavy ring 101 includes first wavy segments located in the region A and second wavy segments located in the region B, where a wave included angle α of each first wavy segment is 70°-120°; the ratio of a wave height L1 of the first wavy segment to a spacing L2 between the adjacent first wavy segments is 1/4-3; a wave included angle α of the second wavy segment is 30°-60°; the ratio of a wave height L3 of the second wavy segment to a spacing L4 between the adjacent second wavy segments is 1/4-3/2; and the ratio of the wave height L1 of the first wavy segment to the wave height L3 of the second wavy segment is greater than or equal to 1/3 and less than 1. The wave included angle α refers to an included angle between supporting bodies 104 connected to two sides of the same proximal vertex 102 or the distal vertex 103.

Figure 3A:
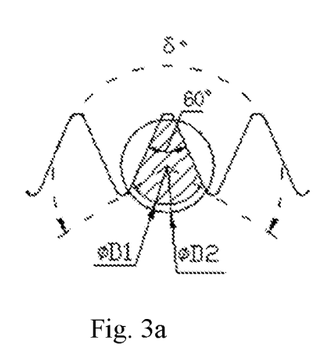
FIG. 3a is a schematic diagram of the stent graft shown in FIG. 1 with a wave included angle being 60°.
Figure 3B:
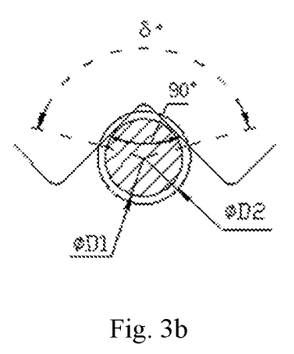
FIG. 3b is a schematic diagram of the stent graft shown in FIG. 1 with a wave included angle being 90°.
Figure 3C:
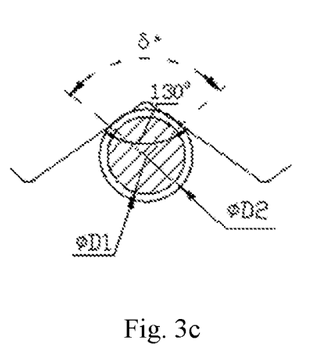
FIG. 3c is a schematic diagram of the stent graft shown in FIG. 1 with a wave included angle being 130°.

When in-situ fenestration is carried out on the stent graft, a puncture component is used to puncture a small hole in the stent graft, and the small hole is dilated to a required size by the use of a balloon. Referring to FIGS. 3a, 3b and 3c, the wave heights of the wavy rings 101 in FIGS. 3a, 3b and 3c are the same, and the wave included angles are 60°, 90° and 130°, respectively. A balloon with a diameter of D1 (such as D1 being 3-18 mm) is used to expand a circle of the same size in the corresponding position of each wavy ring 101, where the corresponding position refers to a position where the distance of a connecting line between the circle center of the balloon and a proximal vertex of the wavy ring 101 in each of FIGS. 3a, 3b and 3c in the axis direction of the stent graft is equal. The hatched lines in the figures indicate the shapes of windows expanded by the balloon, and it can be seen from the figures that when the wave included angle is 90° or 130°, the windows meeting the size requirements may be expanded, while the wavy ring 101 with the wave included angle being 60° may limit the fenestration size so that a fenestration edge follows the wavy ring 101. In the figures, the region of the wavy ring 101 covered by a circle with a diameter of D2 (D2=110% D1) is a region where the wavy ring 101 supports the fenestration edge, that is, the greater the corresponding angle δ of an intersection of the wavy ring 101 and the circle with the diameter of D2 is, the higher the supporting effect that the wavy ring 101 provides for the fenestration edge is. As can be seen from the figures, the larger the wave included angle is, the smaller the corresponding angle δ of the intersection of the wavy ring 101 and the circle with the diameter of D2 is, leading to a failure to provide sufficient support for the fenestration edge by the wavy ring 101.

As can be seen from the above, when the wave included angle of the wavy ring 101 in a certain region is large, the wavy ring 101 does not limit the fenestration size, thereby being beneficial to the fenestration; however, if the wave included angle is too large, the fenestration edge is caused to be far away from the wavy ring 101, and the wavy ring 101 cannot provide enough support for the fenestration edge; and if the fenestration edge lacks the support from the wavy ring 101, the window may be further expanded under the action of radial force of a branch stent, finally leading to the separation of the branch stent from the stent graft. In addition, if the wave included angle of the wavy ring 101 is too large, the number of waves distributed in the circumferential direction of the stent graft in the region is too small, which is not conducive to maintaining the tube cavity shape of the stent graft. However, when the wave included angle of the wavy ring 101 in a certain region is small, although enough support may be provided for the fenestration edge, the fenestration size may be limited, resulting in that the fenestration size hardly meets the size of a branch vessel. In addition, the wavy ring 101 has certain rigidity and is not prone to deformation under the action of external force, and after a fenestration component is abutted against the wavy ring 101, the wavy ring 101 is easily broken or the wavy ring 101 is excessively displaced with respect to the covering membrane 200, so that the radial supporting effect of the stent graft is affected.

According to the embodiments, with the arrangement of the region A and the region B with different wave included angles in the circumferential direction of the stent graft, and the adjustment on the ratio of the wave height of the region A to the wave height of the region B, the region A can meet the requirements of fenestration, and the region B can meet the requirement of axial supporting force, so that the stent graft is prevented from shortening into a tumor cavity. In addition, by adjusting the ratio of the wave height to the wave spacing of the region A and the ratio of the wave height to the wave spacing of the region B, the requirements of fenestration can be well met at each position of the region A, the adaptability of the stent graft is improved, and meanwhile, the situation that the bending property of the stent graft at the position is affected due to dense distribution of local waves in the region A and the region B, or the situation that the stent graft is prone to deformation due to poor the supporting effect of the stent graft in the position caused by sparse distribution of local waves in the region A and the region B, is avoided.

Figure 2:
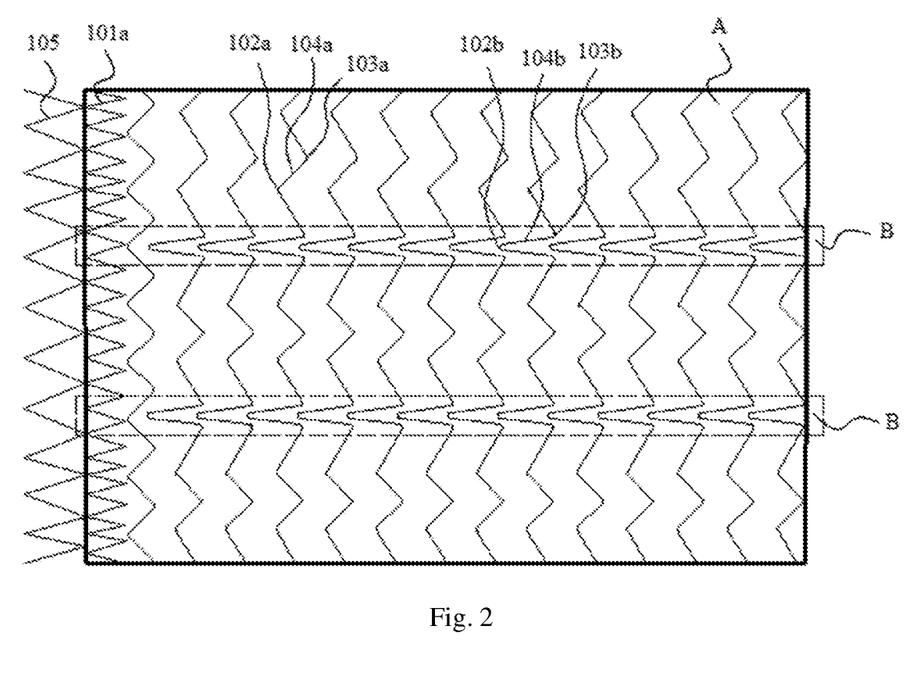
FIG. 2 is a radially expanded view of the stent graft shown in FIG. 1.

Referring to FIG. 2, the first wavy segment includes a plurality of first proximal vertexes 102a, a plurality of first distal vertexes 103a, and first supporting bodies 104a connecting the adjacent first proximal vertexes 102a and first distal vertexes 103a. The second wavy segment includes at least one second proximal vertex 102b, at least one second distal vertex 103b, and a second supporting body 104b connecting the adjacent second proximal vertex 102b and second distal vertex 103b. Here, the wave height L1 of the first wavy segment refers to the distance in the axial direction between the first proximal vertex 102a and the first distal vertex 103a, and the spacing L2 between the adjacent first wavy segments is the distance in the axial direction between the first proximal vertex 102a on the first wavy segment and the first proximal vertex 102a on the adjacent first wavy segment. The wave height L3 of the second wavy segment refers to the distance in the axial direction between the second proximal vertex 102b and the second distal vertex 103b, and the spacing L4 of the adjacent second wavy segments is the distance in the axial direction between the second proximal vertex 102b on the second wavy segment and the second proximal vertex 102b on the adjacent second wavy segment. In the embodiment, the first distal vertex 103a and the second distal vertex 103b are located in the same plane perpendicular to the longitudinal central axis of the stent graft.

When the wave height of the wavy ring 101 is too low, not only is the wave processing not facilitated, but also the radial supporting effect of the stent graft is poor; and when the wave height of the wavy ring 101 is too high, the deformation resistance of the stent graft is poor, and the stent graft is prone to folding. Therefore, L1 and L3 meet the conditions that L1 is greater than or equal to 3 mm and less than or equal to 15 mm and L3 is greater than or equal to 8 mm and less than or equal to 18 mm. For example, L1 is greater than or equal to 6 mm and less than or equal to 12 mm, and L3 is greater than or equal to 12 mm and less than or equal to 14 mm.

Figure 4A:
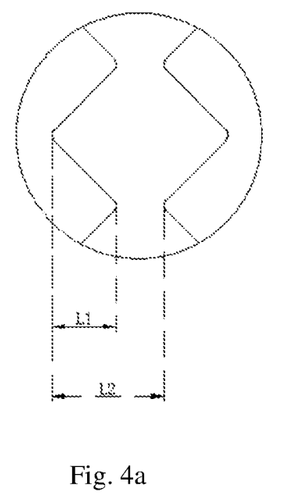
FIG. 4a is a schematic diagram of adjacent first wavy segments of the stent graft shown in FIG. 1 being opposite in phase when the adjacent first wavy segments have no overlap in an axial direction.
Figure 4B:
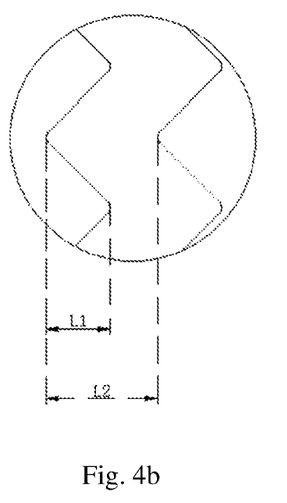
FIG. 4b is a schematic diagram of the adjacent first wavy segments of the stent graft shown in FIG. 1 being identical in phase when the adjacent first wavy segments have no overlap in the axial direction.
Figure 4C:
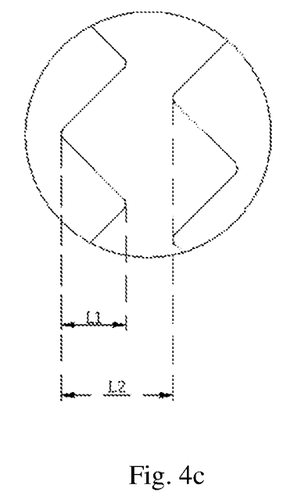
FIG. 4c is a schematic diagram of the adjacent first wavy segments of the stent graft shown in FIG. 1 having a phase difference when the adjacent first wavy segments have no overlap in the axial direction.

A plurality of first wavy segments in the region A are arranged in a spaced manner in the axial direction, and when the adjacent first wavy segments are different in phase, the areas for fenestration between the adjacent first wavy segments are different. FIGS. 4a, 4b and 4c are sequential schematic diagrams of the adjacent first wavy segments being opposite in phase, being identical in phase, and having a phase difference, in the case that the wave structures and wave spacings of the adjacent first wavy segments are identical when the adjacent first wavy segments have no overlap in the axial direction. The state of being opposite in phase means that the wave crests of the first wavy segment are opposite to the wave troughs of the adjacent first wavy segment, the state of being identical in phase means that the wave crests of the first wavy segment are opposite to the wave crests of the adjacent first wavy segment, and the phase difference means that the wave crests of the first wavy segment are staggered with the wave crests and troughs of the adjacent first wavy segment. It can be understood from the figures that when the adjacent first wavy segments are opposite in phase, the area available for fenestration between the adjacent first wavy segments is maximum, and when the adjacent first wavy segments are identical in phase, the area available for fenestration is minimum. However, when the adjacent first wavy segments are identical in phase, the distribution of a fenestration region is relatively uniform.

Figure 5:
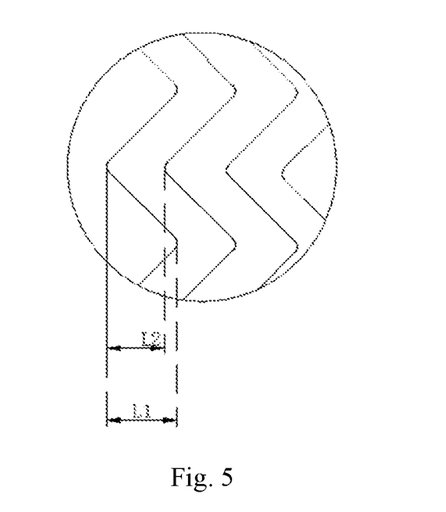
FIG. 5 is a schematic diagram of the adjacent first wavy segments of the stent graft shown in FIG. 1 which have overlaps in the axial direction.

In order to meet the fenestration requirement of the stent graft, different phase conditions can be adapted by adjusting the wave height of the first wavy segment and the ratio of the wave height to the wave spacing. In the case that the adjacent first wavy segments have no overlap in the axial direction, when the connecting line between the wave crest of the first wavy segment and the corresponding wave crest of the adjacent first wavy segment is parallel to the busbar of the stent graft, the value of L1/L2 is greater than or equal to 1/3 and less than or equal to 1, and L1 is greater than or equal to 4 mm and less than or equal to 12 mm; when the connecting line between the wave crest of the first wavy segment and the corresponding wave trough of the adjacent first wavy segment is parallel to the busbar of the stent graft, the value of L1/L2 is greater than or equal to 1/4 and less than or equal to 3/4, and L1 is greater than or equal to 4 mm and less than or equal to 14 mm; and when the connecting line between the wave crest of the first wavy segment and the corresponding wave crest of the adjacent first wavy segment is inclined with respect to the busbar of the stent graft, and the connecting line between the wave trough of the first wavy segment and the corresponding wave trough of the adjacent first wavy segment is also inclined with respect to the busbar of the stent graft, the value of L1/L2 is greater than or equal to 1/4 and less than or equal to 1, and L1 is greater than or equal to 4 mm and less than or equal to 14 mm. As shown in conjunction with FIG. 5, in the case that the adjacent first wavy segments have overlaps in the axial direction, the value of L1/L2 is greater than 1 and less than or equal to 3, and L1 is greater than or equal to 5 mm and less than or equal to 15 mm. The corresponding wave crest here refers to a wave crest of the adjacent first wavy segment, having the shortest connecting distance between which and the wave crest of the first wavy segment than other wave crests of the adjacent first wavy segment; and the corresponding wave trough here refers to a wave trough of the adjacent first wavy segment, having the shortest connecting distance between which and the wave trough of the first wavy segment than other wave troughs of the adjacent first wavy segment.

Figure 6:
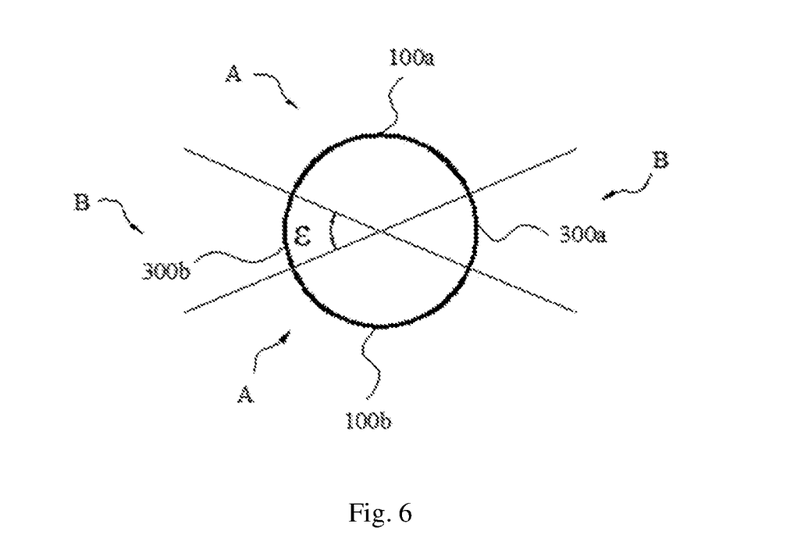
FIG. 6 is a schematic diagram of keel regions of the stent graft shown in FIG. 1 that are distributed on the stent graft.

As shown in FIG. 1 and FIG. 6, the region A includes two sub-regions, namely a greater curvature side region 100*a* and a lesser curvature side region 100*b*, that are distributed in the circumferential direction. Here, the wave included angle of the greater curvature side region 100*a* can be 80°-100°, such as 90°, and the wave included angle of the lesser curvature side region 100*b* can be 75°-95°, such as 80°. The ratio of the wave height of the first wavy segment in the greater curvature side region 100*a* to the wave height of the first wavy segment in the lesser curvature side region 100*b* is about 0.7-1, the ratio of the wave spacing between the adjacent first wavy segments in the greater curvature side region 100*a* to the wave spacing between the adjacent first wavy segments in the lesser curvature side region 100*b* is 0.7-1, and the ratio of the area covered by the greater curvature side region 100*a* on the outer surface of the stent graft to the area covered by the lesser curvature side region 100*b* on the outer surface of the stent graft is 0.7-1.3. In the embodiment, the ratio of the area covered by the greater curvature side region 100*a* on the outer surface of the stent graft is equal to the area covered by the lesser curvature side region 100*b* on the outer surface of the stent graft, the wave heights of the first wavy segments in the greater curvature side region 100*a* are equal, and the wave spacings between the adjacent first wavy segments in the greater curvature side region 100*a* are equal. Also, the wave heights of the first wavy segments in the lesser curvature side region 100*b* are equal, and the wave spacings between the adjacent first wavy segments in the lesser curvature side region 100*b* are equal.

In the embodiment, the greater curvature side region 100*a* and the lesser curvature side region 100*b* are disposed oppositely in the circumferential direction, and the region B is connected between the greater curvature side region 100*a* and the lesser curvature side region 100*b*. It can be appreciated that the region A may also include three or more circumferentially distributed sub-regions as desired, the sub-regions may be arranged in a spaced manner or continuously, and the wave shapes, the number of waves, the wave heights, and the wave angles of the wavy segments of each sub-region may be set as desired.

Further, the axial shortening rate of the region B is less than the axial shortening rate of the region A, and the axial shortening rate of the stent graft in the region B is 10%-40%.

A method for calculating the shortening rate of the stent graft in the axial direction is as follows: taking the length of the stent graft, which is in a straight tube shape, in the axial direction in a natural state as r and the diameter of the stent graft as d1, sleeving an inner tube with the diameter of d2 (d2 is less than d1, for example, d2 is equal to 90%*d1) with the stent graft, applying pressure F ($1N \leq F \leq 2N$) in the axial direction to the stent graft till the stent graft cannot shorten anymore to obtain the total length s, and calculating the axial shortening rate of the stent graft in the region B according to the formula $(r-s)/r \times 100\%$. Here, the value of $(r-s)$ can be an available maximum shortening value of the stent graft. The stent graft sleeves the inner tube for shortening, so that the phenomenon that the stent graft is folded when shortening can be effectively avoided, that is, the value of $(r-s)$ is the available maximum shortening value when the stent graft is not folded.

When the stent graft is in a frustum shape, that is, the diameters of the two ends of the stent graft are different, the length of the stent graft in the axial direction in the natural state is r, the diameter of the large end is d1, the diameter of the small end is d3, the stent graft sleeves a conical inner tube or a frustum inner tube with the same taper as the stent graft, and the perpendicular distance between the stent graft and the conical inner tube or the frustum inner tube is 0.05d1. The position of the small end of the stent graft is fixed and unchanged, the pressure F ($1N \leq F \leq 2N$) in the axial direction is applied to the large end, and the total length of the stent graft when the stent graft cannot shorten anymore is s, and thus the shortening rate of the stent graft in the axial direction is $(r-s)/r\ 100\%$. Here, the value of $(r-s)$ is an available maximum shortening value of the stent graft. The stent graft sleeves the inner tube for shortening, so that the phenomenon that the stent graft is folded when shortening can be effectively avoided, that is, the value of $(r-s)$ is the available maximum shortening value when the stent graft is not folded.

Figure 7:
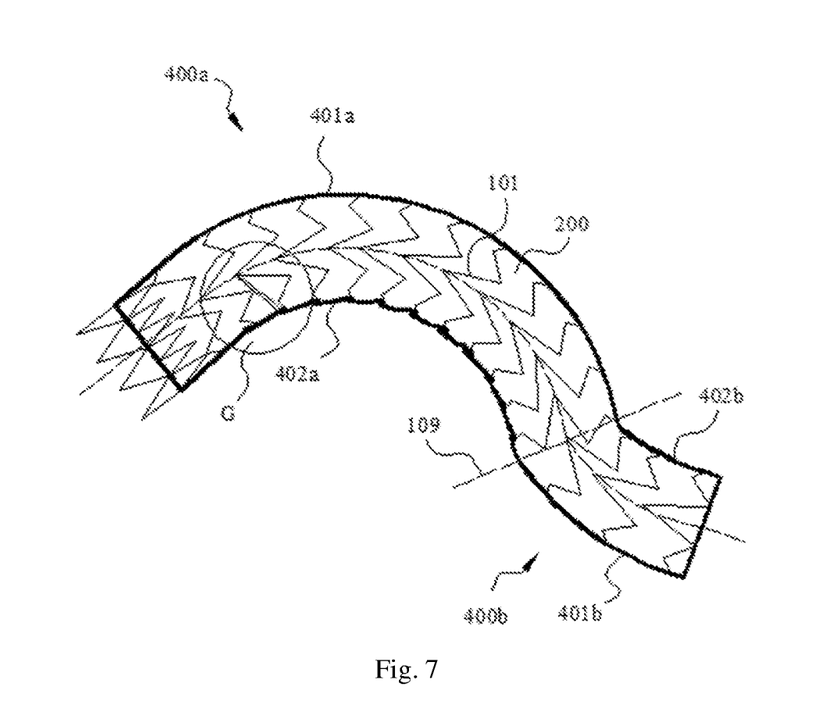
FIG. 7 is a structural schematic diagram of a bent stent graft provided by a first exemplary embodiment.
Figure 8:
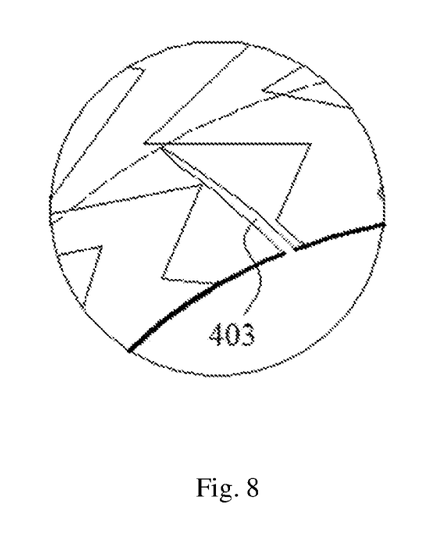
FIG. 8 is an enlarged view of a portion G of the stent graft shown in FIG. 7.
Figure 9:
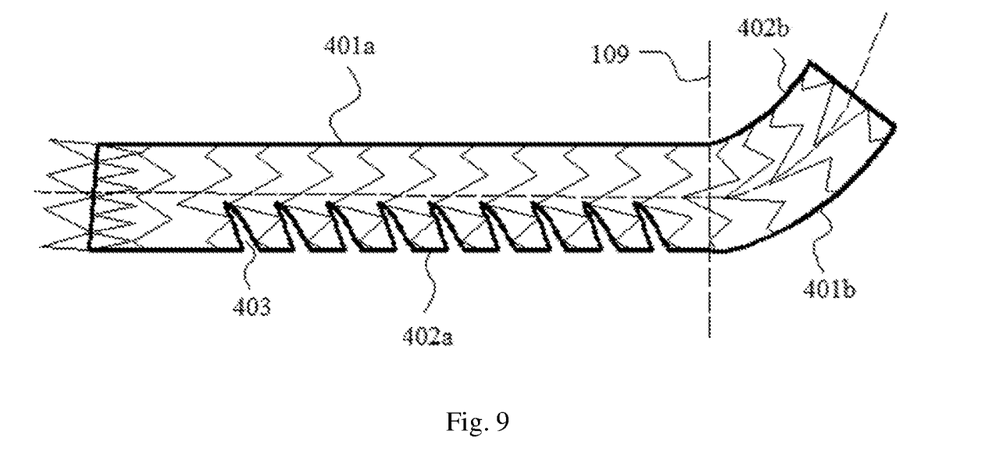
FIG. 9 is a structural schematic diagram of a first bent section of the stent graft shown in FIG. 7 after being straightened along a first profile line.
Figure 10:
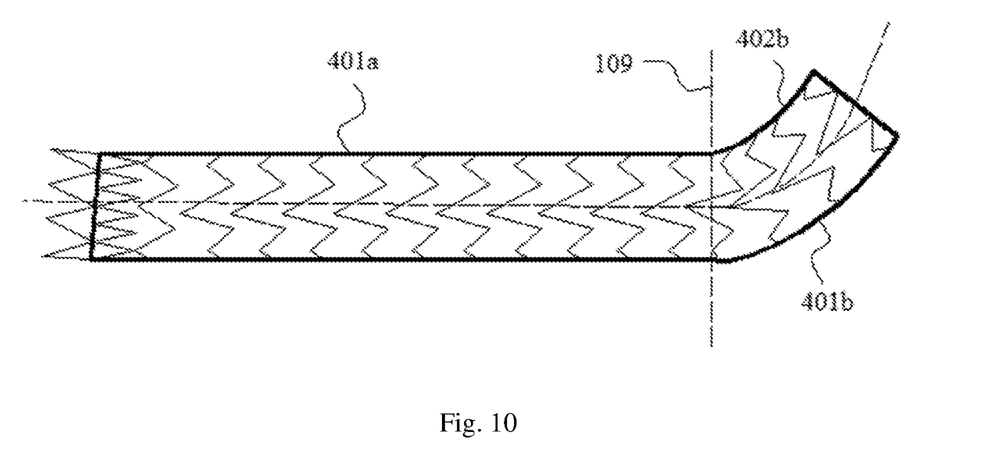
FIG. 10 is a structural schematic diagram of wavy rings of the stent graft shown in FIG. 7 after being re-arranged in the axial direction according to the wave spacing at the first profile line and covered with membranes.

When the stent graft itself is manufactured into a bent shape, as shown in FIG. 7, the stent graft includes a first bent section 400*a* and a second bent section 400*b*, the first bent section 400*a* has a first profile line 401*a* on a greater curvature side of the first bent section 400*a* and a second profile line 402*a* on a lesser curvature side of the first bent section 400*a*, and the second bent section 400*b* has a third profile line 401*b* on a greater curvature side of the second bent section 400b and a fourth profile line 402b on a lesser curvature side of the second bent section 400b. At this time, there are several methods for calculating the shortening rate of the bent section of the stent graft. One method is as follows: referring to FIG. 8 together, by taking the first bent section 400a as an example, partitioning the first bent section 400a with a plane 109 perpendicular to the axial direction of the stent graft; cutting a plurality of notches 403 in the covering membranes 200 close to the second profile line 402a, where the sizes of the notches 403 can ensure that the stent graft is straightened along the first profile line 401a (or cutting a plurality of notches 403 in the covering membranes 200 close to the second profile line 402a, where the sizes of the notches 403 can exactly ensure that the stent graft is straightened along the first profile line 401a); after the first bent section 400a is straightened as shown in FIG. 9, obtaining the length r and the diameter d1 of the straightened first bent section 400a; sleeving an inner tube with a diameter of d2 (d2 is less than d1, for example, d2 is equal to 90%*d1) with the straightened first bent section 400a; applying pressure F (1N≤F≤2N) in the axial direction to the stent graft till the stent graft cannot shorten to obtain the total length s of the region B; and calculating the axial shortening rate of the stent graft in the region B according to the formula (r−s)/r*100%. Another method is as follows: also by taking the first bent section 400a as an example, re-arranging the wavy rings 101 in the axial direction according to the wave spacing between the wavy rings 101 at the first profile line 401a, covering the wavy rings 101 with membranes (covering materials and a selected process are kept consistent with those of the original stent), as shown in FIG. 10, and then calculating the shortening rate according to the above-mentioned method for calculating the shortening rate.

Figure 11:
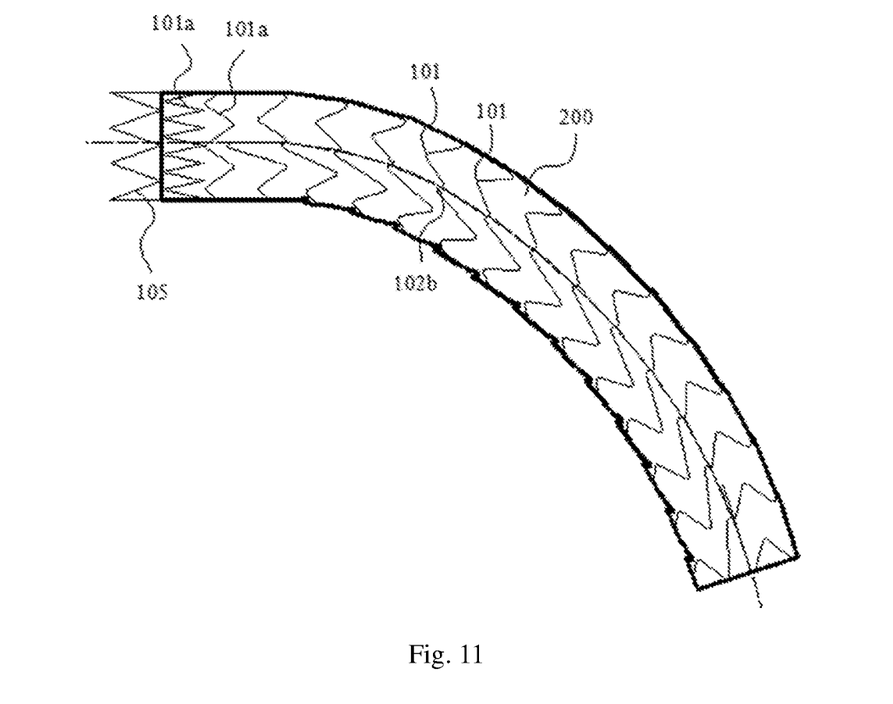
FIG. 11 is a structural schematic diagram of the wavy rings of the stent graft shown in FIG. 1 which abut against mutually.

During the bending of the stent graft, when any one of the region B or the region A reaches the available maximum shortening value, a rigid axial supporting structure is formed in the region, so that the stent graft cannot continue to be bent. Referring to FIG. 11, during the bending of the stent graft, one wavy ring 101 of the stent graft moves in the direction of pressure together with portions of the covering membranes 200 fixed to the wavy ring 101, the portions of the covering membranes 200 fixed to the wavy ring 101 move together with portions of the covering membranes 200 distributed at the periphery of the wavy ring 101, immediately the portions of the covering membranes 200 distributed at the periphery of the wavy ring 101 pull another wavy ring 101 nearby to move towards one side close to the wavy ring 101 till the wavy ring 101 cannot keep moving, and at this time a rigid axial supporting structure is formed on the stent graft, so that the stent graft is prevented from continuing to shorten anymore.

When the axial shortening rate of the stent graft in the region B is less than 10%, the shortening rate of the region B is too small, and no matter to which direction the stent graft is bent, the region B easily reaches the available maximum shortening value, and the region B cannot shorten anymore, thereby restricting the stent graft from continuing to be bent. When the axial shortening rate of the stent graft in the region B is greater than 40%, the axial supporting effect of the stent graft is poor, and the stent graft may enter the tumor cavity when the distal end of the stent graft shortens towards the proximal end of the stent graft, thus threatening the life of a patient. When the shortening rate of the stent graft in the region B is 10%-40%, the stent graft can be bent towards all directions to adapt to bent blood vessels, and sufficient axial supporting force can be provided for the stent graft to achieve the axial shortening prevention effect, thus maintaining the tube cavity shape of the stent graft. Referring to FIG. 7, the stent graft may be continuously bent towards different directions to better adapt to a bent blood vessel. For example, the axial shortening rate of the stent graft in the region B is 20%-30%.

Referring to FIG. 6, the circumferential angle covered by the region B on an outer surface of the stent graft is c° which is greater than or equal to 15° and less than or equal to 90°. When c° is less than 15°, the circumferential angle covered by the region B on the outer surface of stent graft is small, so that poor axial supporting effect of the entire stent graft may be caused, and the stent graft may easily swing and retract under the impact of a blood flow, finally causing the stent graft to retract into the tumor cavity, and endangering the life of the patient; and when c° is greater than 90°, the circumferential angle covered by the region B on the outer surface of the stent graft is large, which is not conducive to stent bending. When c° is greater than or equal to 15° and less than or equal to 90°, sufficient axial support can be provided for the stent graft, and when the stent graft is applied to a more bent blood vessel, no folding occurs, thereby keeping the tube cavity smooth, and enabling the stent graft to adapt to a wider range of vascular morphology.

In this embodiment, the region B includes two keel regions in the circumferential direction, namely a first keel region 300a and a second keel region 300b, which are located between the greater curvature side region 100a and the lesser curvature side region 100b, respectively. Circumferential angles covered by the first keel region 300a and the second keel region 300b on the outer surface of the stent graft are 15°-45°, such as about 20°-30°, and the circumferential angles covered by the first keel region 300a and the second keel region 300b may be identical or different. It can be appreciated that the region B may also include three or more keel regions as desired, the keel regions may be arranged in a spaced manner or continuously, and the wave shapes, the number of waves, the wave heights, and the wave angles of the wavy segments of each keel region may be set as desired.

In the embodiment, the second wavy segment includes a second proximal vertex 102b, and the connecting line between the second proximal vertexes 102b of the adjacent second wavy segments is parallel to the axis of the stent graft.

Further, referring to FIGS. 1 and 2, at least one proximal wavy ring 101a is disposed at one end of the plurality of wavy rings 101.

Here, the wave included angle of the proximal wavy ring 101a can be 30°-60°, the waves of the proximal wavy ring 101a and the wavy rings 101 can be the same, and both can be V-shaped, Z-shaped, M-shaped, or the like, and the number of the waves of the proximal wavy ring 101a in the circumferential direction can be greater than the number of the waves of the wavy ring 101 in the circumferential direction. Due to the fact that the proximal wavy rings 101a located at an end portion of the stent graft has a greater number of waves in the circumferential direction, the radial supporting force of the end portion of the stent graft is high, and the wall adhering effect of the end portion of the stent graft may be effectively improved.

It can be appreciated that at least one distal wavy ring (not shown) is also disposed at the other end of the plurality of wavy rings 101, the wave included angle of the distal wavy ring is 50°-70°, the waves of the distal wavy ring and the wavy rings 101 are the same, and both are V-shaped, Z-shaped, M-shaped, or the like, and the number of the waves of the distal wavy ring in the circumferential direction is greater than the number of the waves of the wavy ring 101 in the circumferential direction. Here, both the proximal wavy ring and the distal wavy ring can be made of materials having good biocompatibility, such as nickel titanium, stainless steel or the like. The proximal wavy ring and the distal wavy ring are both of closed cylindrical structures. The proximal wavy ring and the distal wavy ring may be of Z-shaped wave, M-shaped wave, V-shaped wave or sinusoidal wave structures, or of other structures that are radially compressible to a very small diameter. It can be appreciated that not only the numbers of the proximal wavy ring and the distal wavy ring may be set as desired, but also the wave shapes, the number of waves, and the wave heights of the proximal wavy ring and the distal wavy ring may be set as desired.

Further, the stent graft further includes an anchoring bare stent 105 located at one or two ends of the stent graft and connected with the proximal wavy ring or the distal wavy ring.

Figure 12:
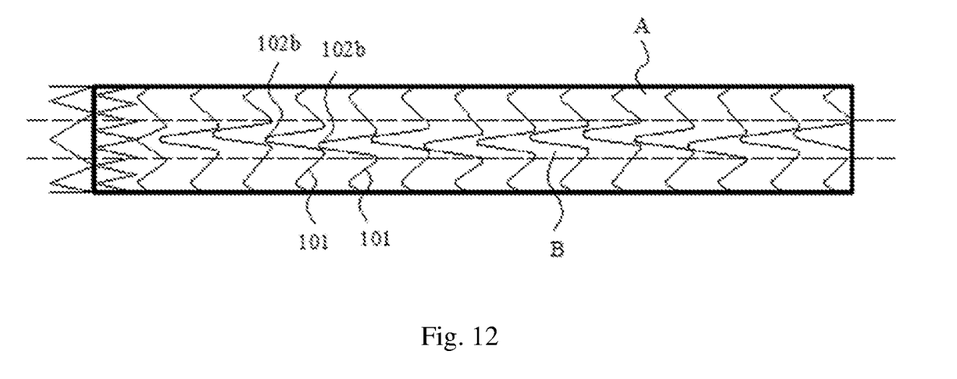
FIG. 12 is a schematic diagram of a stent graft provided by a second exemplary embodiment.

FIG. 12 shows a stent graft provided by a second exemplary embodiment, which differs from the first embodiment in that a connecting line between the second proximal vertexes 102b of the adjacent second wavy segments is disposed obliquely with respect to the axis of stent graft.

Figure 13:
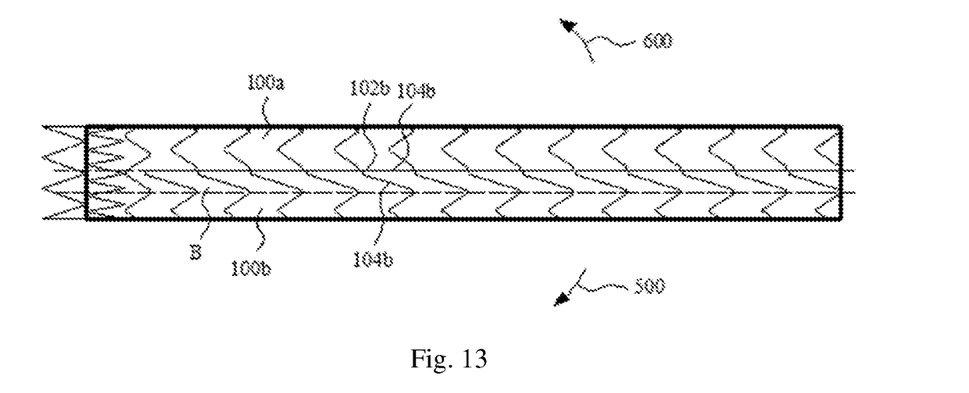
FIG. 13 is a structural schematic diagram of a stent graft provided by a third exemplary embodiment.

FIG. 13 shows a stent graft provided by a third exemplary embodiment, which differs from the first embodiment in that the second supporting bodies 104b that are connected to one sides of the second proximal vertexes 102b and close to the greater curvature side region 100a are distributed in the direction parallel to the axial direction of the stent graft, and the second supporting bodies 104b that are connected to the other sides of the second proximal vertexes 102b and close to the lesser curvature side region 100b are disposed obliquely with respect to the axis direction of the stent graft.

Figure 14:
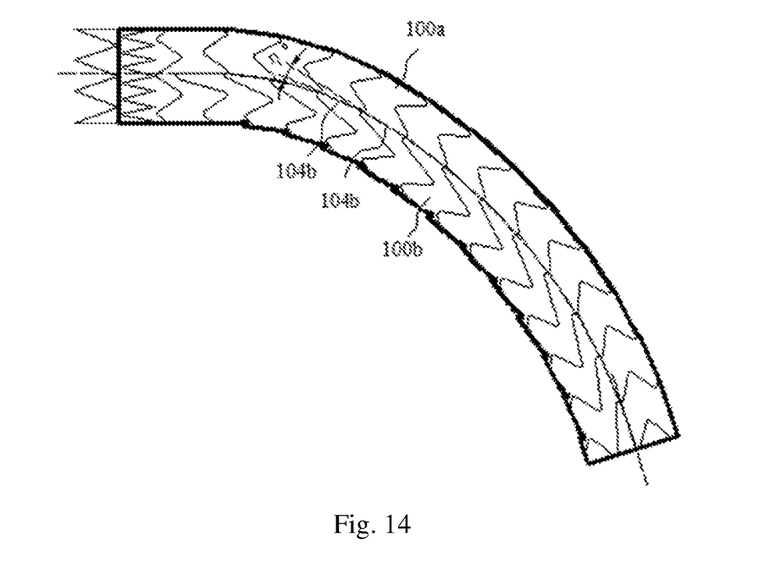
FIG. 14 is a structural schematic diagram of the stent graft shown in FIG. 13 after being bent in a direction indicated by a first arrow.
Figure 15:
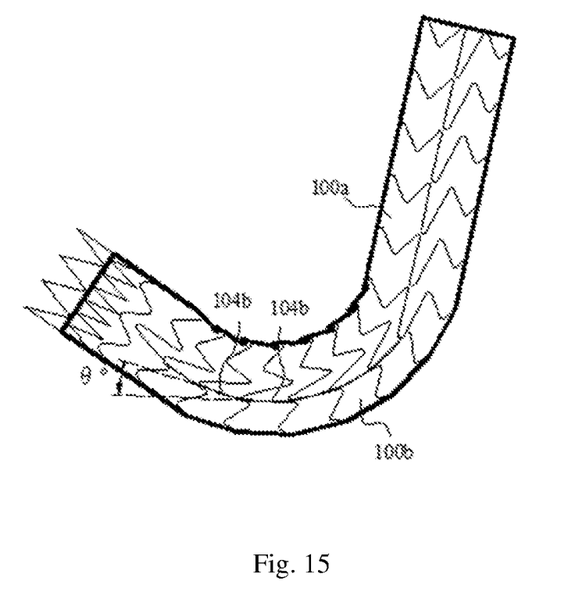
FIG. 15 is a structural schematic diagram of the stent graft shown in FIG. 13 after being bent in a direction indicated by a second arrow.

When the stent graft shown in FIG. 13 is bent in a direction indicated by a first arrow 500, referring to FIG. 14, the second supporting bodies 104b, adjacent to the greater curvature side region 100a, of the adjacent second wavy segments abut against mutually to form axial support, and the included angle between the second supporting bodies 104b, adjacent to the greater curvature side region 100a, of the adjacent second wavy segments is η°. When the stent graft of FIG. 13 is bent in a direction indicated by a second arrow 600, referring to FIG. 15, the second supporting bodies 104b, adjacent to the lesser curvature side region 100b, of the adjacent second wavy segments abut against mutually to form axial support, and the included angle between the second supporting bodies 104b, adjacent to the lesser curvature side region 100b, of the adjacent second wavy segments is θ°. As can be seen from the figures, η is less than θ°. When the second supporting bodies 104b of the adjacent second wavy segments abut against mutually to form the axial support, the greater the included angle between the second supporting bodies 104b of the adjacent second wavy segments is, the smaller the force divided to the axial direction of the stent graft is, and the poorer the axial supporting effect on the stent graft is. Therefore, the axial supporting effect formed when the second supporting bodies 104b distributed in the direction parallel to the axial direction of the stent graft abut against mutually in FIG. 14 is superior to the axial supporting effect formed when the second supporting bodies 104b disposed obliquely with respect to the axis direction of the stent graft abut against mutually in FIG. 15. Meanwhile, when the included angle between the second supporting bodies 104b of the adjacent second wavy segments is greater, excessive deformation of the covering membranes of the keel regions is easily caused to bring about an uneven surface of the stent graft, thus leading to high probability of thrombosis.

When the second supporting bodies 104b distributed in the direction parallel to the axial direction of the stent graft abut against mutually to form the axial support, the greater the included angle between the second supporting bodies 104b of the adjacent second wavy segments is, the higher the axial supporting force of the stent graft is. Therefore, the second supporting bodies 104b distributed in the direction parallel to the axial direction of the stent graft are disposed on one side close to the greater curvature side region 100a, and when the stent graft is bent towards the lesser curvature side, the second supporting bodies 104b may provide enough axial supporting force for the stent graft, and the axial supporting effect on the stent graft is optimal.

The features of the above-mentioned embodiments may be combined in any combination. In the interest of brevity, all possible combinations of the features in the above embodiments are not described, but all should be considered as within the scope of the embodiments, except combinations where at least some of such technical features are mutually exclusive.

The above-mentioned embodiments are merely illustrative of several embodiments of the present application, and the description thereof is more specific and detailed, but should not to be construed as limiting the scope of protection. It should be noted that several modifications and improvements can be made by persons of ordinary skill in the art without departing from the concept of the present application.

The invention claimed is:

1. A stent graft, comprising:
   a plurality of wavy rings, the stent graft further comprising, along a circumferential direction, a first region and a second region connected with the first region;
   each wavy ring comprises first wavy segments located in the first region and second wavy segments located in the second region;
   a wave included angle of each first wavy segment ranges from 70° to 120°;
   the ratio of a wave height (L1) of the first wavy segment to a spacing (L2) between the adjacent first wavy segments ranges from 1/4 to 3;
   a wave included angle of each second wavy segment ranges from 30° to 60°;
   the ratio of a wave height of the second wavy segment to a spacing between the adjacent second wavy segments ranges from 1/4 to 3/2; and
   the ratio of the wave height of the first wavy segment to the wave height of the second wavy segment is greater than or equal to 1/3 and less than 1; wherein
   the wave height of the first wavy segment is the distance in an axial direction of the stent graft between a first proximal vertex of the first wavy segment and a first distal vertex of the first wavy segment,
   the spacing between the adjacent first wavy segments is the distance in the axial direction of the stent graft between the first proximal vertex of the first wavy segment and a first proximal vertex of an adjacent first wavy segment,
   the wave height of the second wavy segment is the distance in the axial direction of the stent graft between a second proximal vertex of the second wavy segment and a second distal vertex of the second wavy segment, and
   the spacing of the adjacent second wavy segments is the distance in the axial direction of the stent graft between the second proximal vertex of the second wavy segment and a second proximal vertex of an adjacent second wavy segment;

wherein a connecting line between adjacent wave crests of the first wavy segment and a connecting line between adjacent wave crests of the second wavy segment are both perpendicular to the axial direction of the stent graft.

2. The stent graft of claim 1, wherein the first region comprises a greater curvature side region and a lesser curvature side region that are distributed along the circumferential direction, the wave included angle of the greater curvature side region ranges from 80° to 100°, and the wave included angle of the lesser curvature side region ranges from 75° to 95°.

3. The stent graft of claim 2, wherein the ratio of the wave height of the first wavy segment in the greater curvature side region to the wave height of the first wavy segment in the lesser curvature side region ranges from 0.7 to 1.

4. The stent graft of claim 2, wherein the ratio of the wave spacing of the adjacent first wavy segments in the greater curvature side region to the wave spacing between the adjacent first wavy segments in the lesser curvature side region ranges from 0.7 to 1.

5. The stent graft of claim 2, wherein the ratio of the area covered by the greater curvature side region on an outer surface of the stent graft to the area covered by the lesser curvature side region on the outer surface of the stent graft ranges from 0.7 to 1.3.

6. The stent graft of claim 2, wherein the greater curvature side region and the lesser curvature side region are symmetrically disposed in the circumferential direction, and the second region is located between the greater curvature side region and the lesser curvature side region.

7. The stent graft of claim 1, wherein an included angle of the second region in the circumferential direction ranges from 15° to 90°.

8. The stent graft of claim 1, wherein, when a connecting line between a wave crest of the first wavy segment and a corresponding wave crest of the adjacent first wavy segment is parallel to the axial direction of the stent graft, the value of L1/L2 is greater than or equal to 1/3 and less than or equal to 1, and L1 is greater than or equal to 4 mm and less than or equal to 12 mm.

9. The stent graft of claim 8, wherein, when a connecting line between the wave crest of the first wavy segment and a corresponding wave trough of the adjacent first wavy segment is parallel to the axial direction of the stent graft, the value of L1/L2 is greater than or equal to 1/4 and less than or equal to 3/4, and L1 is greater than or equal to 4 mm and less than or equal to 14 mm.

10. The stent graft of claim 1, wherein the wave height of the first wavy segment ranges from 3 to 15 mm, and the wave height of the second wavy segment ranges from 8 to 18 mm.

* * * * *